US00PP11881P2

(12) United States Plant Patent
Dubois et al.

(10) Patent No.: US PP11,881 P2
(45) Date of Patent: May 22, 2001

(54) ROSE PLANT NAMED 'IVTAHOCKEY'

(75) Inventors: L. A. M. Dubois, Wageningen; D. P. De Vries, Ede, both of (NL)

(73) Assignee: Stichting DLO-Centrum voor Plantenveredelings- en Reproduktieonderzoek (NL)

( * ) Notice: Subject to any disclaimer, the term of this patent is extended or adjusted under 35 U.S.C. 154(b) by 0 days.

(21) Appl. No.: 09/079,737

(22) Filed: May 15, 1998

(51) Int. Cl.[7] ..... A01H 5/00
(52) U.S. Cl. ..... Plt./122
(58) Field of Search ..... Plt./107, 108, 121, Plt./122, 116

*Primary Examiner*—Howard J. Locker
(74) *Attorney, Agent, or Firm*—Webb Ziesenheim Logsdon Orkin & Hanson, P.C.

(57) ABSTRACT

The new cultivar is a variety of dwarf rose plant having a broad bushy growth habit. The semi-double flowers are very small and light red/deep pink in color.

3 Drawing Sheets

BACKGROUND OF THE NEW PLANT

This discovery relates to a new and distinct variety of patio rose plant identified by the varietal name of 'Ivtahockey'. The new variety was discovered in a selected breeding program at Stichting DLO-Centrum voor Plantenveredelings- en Reproduktieonderzoek (CPRO-DLO) in Wageningen, The Netherlands in 1984. The goal of the breeding program was to develop cultivars of pot roses and patio roses. The new variety is a selection from the crossing of 'Amanda' with a breeding variety of *R. multiflora*×'White Spray'.

The first asexual reproduction took place at Stichting DLO-Centrum voor Plantenveredelings- en Reproduktieonderzoek (CPRO-DLO) in Wageningen, The Netherlands in 1990 and the new variety has been propagated by cutting, stenting (rooting and grafting in a single procedure) and grafting on *R. dumetorum* 'laxa'. Continued observations from the vegetative cuttings have confirmed that the distinguishing features of this new cultivar remain stable and are retained through successive propagations.

The new variety is highly resistant to black spot and mildew and is compact with abundant flowering.

DESCRIPTION OF THE DRAWINGS

The accompanying photographic drawings illustrates the new variety with the color being as nearly true as is possible with color illustrations of this type.

DESCRIPTION OF THE NEW PLANT

Figure 1:
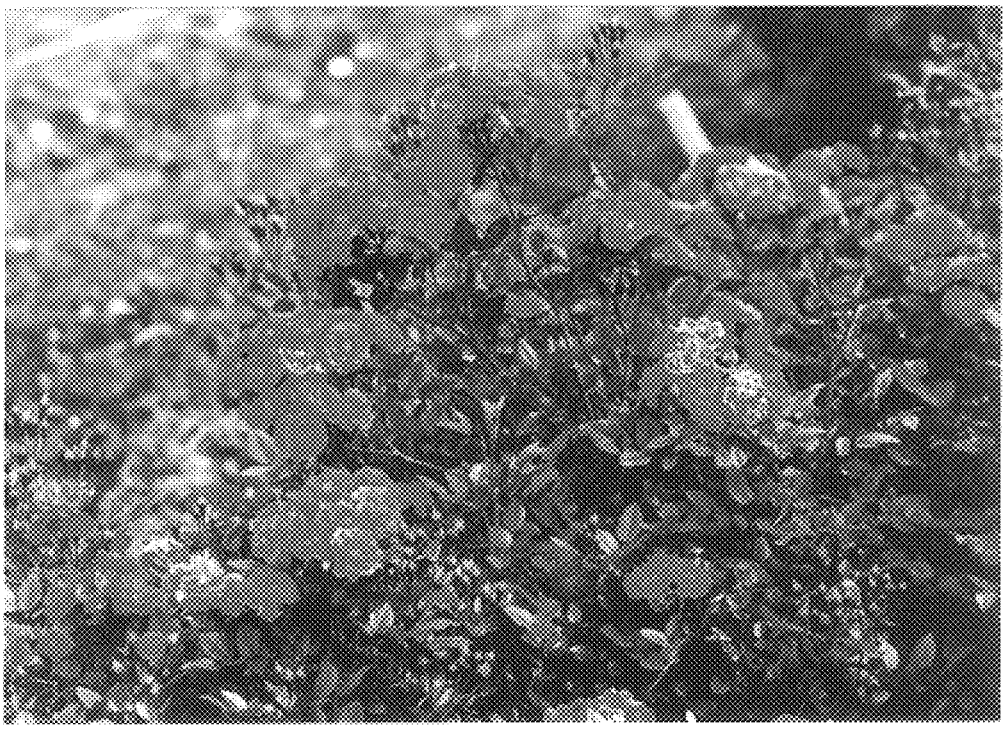
FIG. 1 shows the overall plant.
Figure 2:
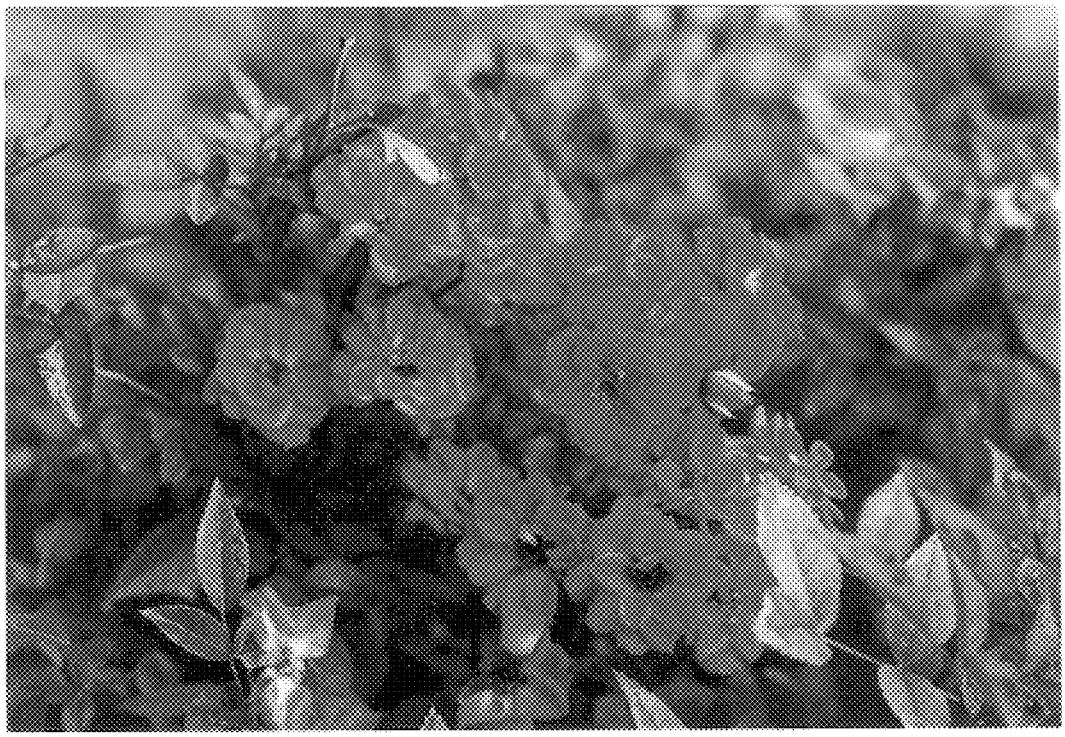
FIG. 2 is a close-up view of the buds and bloom of the plant.
Figure 3:
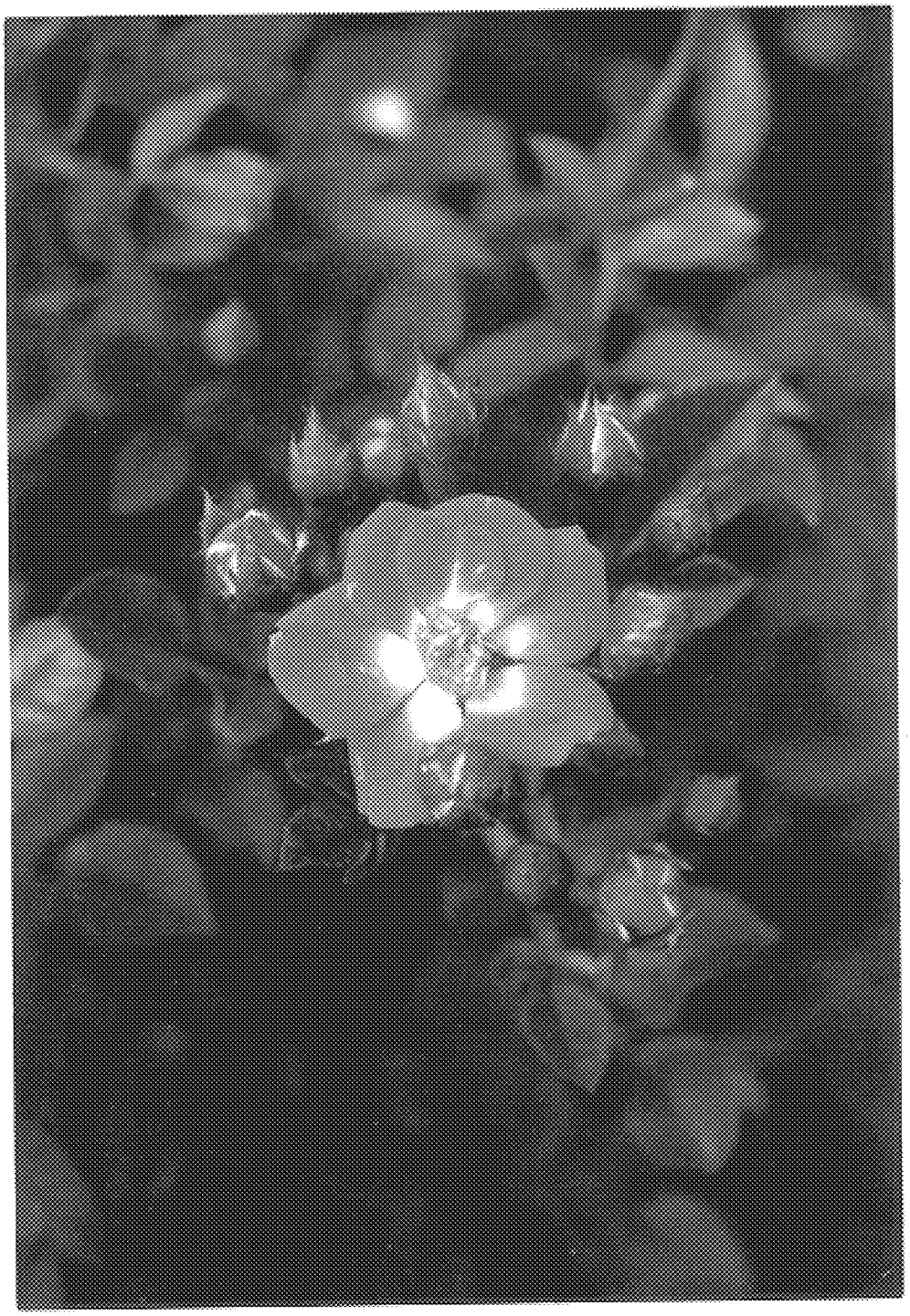
FIG. 3 is another close-up view of the buds and bloom of the plant.

The following detailed descriptions set forth the characteristics of the new variety. The data which define these characteristics were collected from asexual reproductions carried out at Stichting DLO-Centrum voor Plantenveredelings- en Reproduktieonderzoek (CPRO-DLO) in Wageningen, The Netherlands. Color references are primarily to The R.H.S. Colour Chart of The Royal Horticultural Society of London.

PLANT

Varietal name: Ivtahockey.
Commercial name: Hockey.
Botanical name: *Rosa l.*
Size:
- *Height.*—40–50 cm.
- *Width.*—30–40 cm.

Habit: Compact.
Growth vigor: Vigorous.
Wood color: Green group 137B.
Thorns:
- *Color.*—Green Group 137C.
- *Size.*—About 0.5 cm long.
- *Shape.*—Concave, curved downwardly.
- *Location on stem and branches.*—Very few on main canes from base, very few on stems and branches, equally divided between the stems and branches.

Disease resistance: Under normal conditions (no long periods of coldness, dryness, or wetness), resistant to black spot and mildew.
Hardiness: Survived the last three winters in The Netherlands.

FOLIAGE

Arrangement: Compound.
Size: 7.0×9.0 cm.
Color when juvenile: Green group 137A.
Leaflets:
- *Number on typical stem leaves.*—5–7.
- *Size.*—About 3.5 by 1.5 cm.
- *Color.*—Upper surface: Green Group 137A. Lower surface: Green Group 137C.
- *Shape.*—Ovate.
- *Texture.*—Upper side, glossy.
- *Margin.*—Single, very small serrations.
- *Petiole rachis.*—Color: Green Group 143A. Texture: Small glands along the side.
- *Stipules.*—Present on mature compound leaf, serrated.

BUDS

Size: About 1.0 cm by 0.6 cm.
Shape: Ovate.
Color: Green Group 143B.

Color changes during opening: None.
Sepals:
*Color.—Upper surface: Green group* 143B.
*Lower surface: Yellow-green group* 144A.
*Texture.*—Covered with fine hairs.
*Foliation.*—Slight.
Receptacle:
*Color.*—Green group 143B.
*Shape.*—Pear shaped.
*Texture.*—Smooth.
Peduncle:
*Color.*—Green group 143B.
*Length.*—About 4.0 cm.
*Strength.*—Stiff, erect.
*Texture.*—Smooth.

FLOWER

Borne: 30–35 per cluster.
Size: About 3.0 cm in diameter.
Form: Double flowered.
Petals:
*Number per flower.*—About 25.
*Color.*—Upper surface: Red Group 47B. Lower surface: Red Group 47B. Color changes with maturity: Some variation of color upon aging of the blooms.
Texture: Thick. Size: About 1.5 cm by 1.0 cm. Shape: Ovate. Arrangement: Imbricated. Persistence: Petals tend to detach fairly cleanly. Lastingness: About 7 days.
Fragrance: Slight.
Blooming period: At least 7–10 days.

REPRODUCTIVE ORGANS

Stamens:
*Number.*—60–70 per flower.
*Anther.*—Length: About 1.0 mm. Color: Yellow-Orange Group 15B. Pollen Color: Yellow Group llC.
*Filament.*—Length: About 5 mm. Color: Yellow Group 11B.
Pistils:
*Number.*—25 per flower.
*Style.*—Color: Green-Yellow Group 1C. Length: About 0.7 cm.
*Stigma.*—Color: Green-Yellow Group 1B. Length: Less than 1.0 mm.

I claim:

1. A new and distinct variety of rose plant substantially as shown and described.

* * * * *